(12) United States Patent
Lopatin

(10) Patent No.: US 7,191,638 B2
(45) Date of Patent: Mar. 20, 2007

(54) DEVICE FOR DETERMINING AND/OR MONITORING AT LEAST ONE PHYSICAL PARAMETER AND HAVING A PIEZO-DRIVE FOR OSCILLATION-EXCITATION AND -DETECTION

(75) Inventor: Sergej Lopatin, Lörrach (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 72 days.

(21) Appl. No.: 10/739,526

(22) Filed: Dec. 19, 2003

(65) Prior Publication Data

US 2005/0034521 A1    Feb. 17, 2005

(30) Foreign Application Priority Data

Dec. 19, 2002  (DE) ............................... 102 60 088

(51) Int. Cl.
*G01N 11/10*  (2006.01)
(52) U.S. Cl. .................... 73/24.06; 73/24.05; 73/31.06; 73/32 A; 73/54.26; 73/54.41; 73/61.49; 73/64.53; 73/579
(58) Field of Classification Search .................... None
See application file for complete search history.

(56) References Cited

U.S. PATENT DOCUMENTS

| | | | | |
|---|---|---|---|---|
| 4,811,593 A | * | 3/1989 | Miura et al. ................ | 73/54.26 |
| 4,879,909 A | * | 11/1989 | Lew .......................... | 73/861.24 |
| 4,934,194 A | * | 6/1990 | Itoh et al. ................. | 73/861.22 |
| 4,986,134 A | * | 1/1991 | Lew .......................... | 73/861.24 |
| 5,121,658 A | * | 6/1992 | Lew ............................. | 73/195 |
| 6,148,665 A | | 11/2000 | Getman et al. | |
| 6,326,563 B1 | * | 12/2001 | Takeuchi et al. ........ | 177/210 FP |
| 6,386,053 B1 | * | 5/2002 | Takeuchi et al. .............. | 73/865 |

FOREIGN PATENT DOCUMENTS

WO    WO 01/85236 A2    11/2001

* cited by examiner

*Primary Examiner*—Hezron Williams
*Assistant Examiner*—Rose M. Miller
(74) *Attorney, Agent, or Firm*—Bacon & Thomas, PLLC

(57) ABSTRACT

A device for determining and/or monitoring at least one physical parameter of a medium, having at least one mechanically oscillatable unit and at least one drive-/receive unit. The drive-/receive unit excites the oscillatable unit to oscillate, or, it receives the oscillations of the oscillatable unit, as the case may be. The invention includes that in the drive-/receive unit at least one piezo-drive is provided, which has at least one exterior surface. The exterior surface is composed of at least two segments of different polarization, wherein the directions of polarization are directed essentially opposite to one another. The mechanically oscillatable unit is directly or indirectly connected with the exterior surface, so that the mechanically oscillatable unit is excited to a movement, or so that the movement of the mechanically oscillatable unit is received. The movement always has at least two different force components.

19 Claims, 6 Drawing Sheets

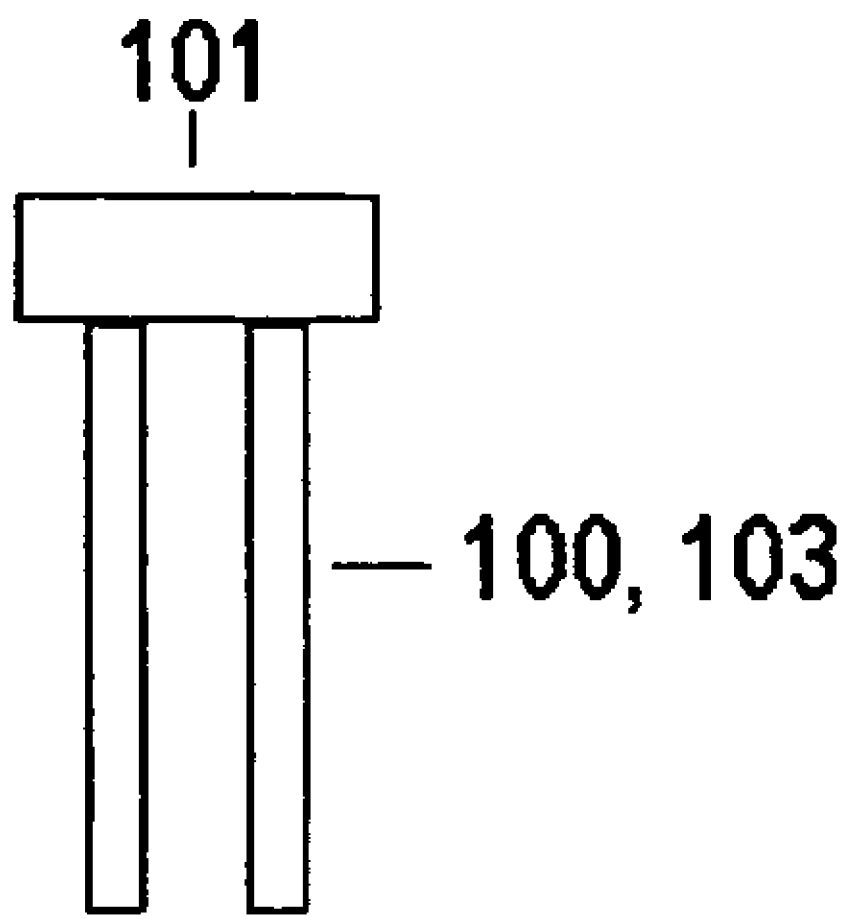

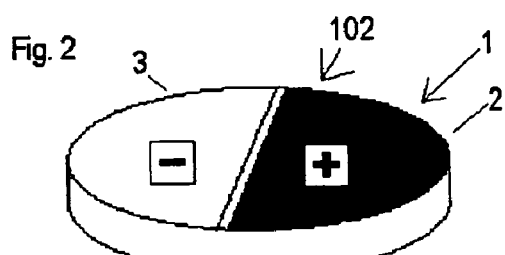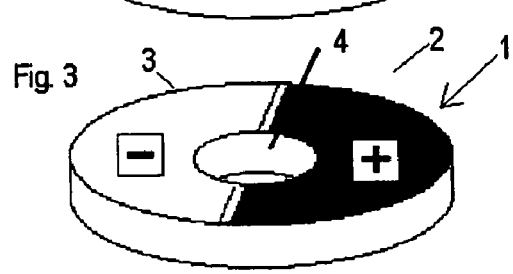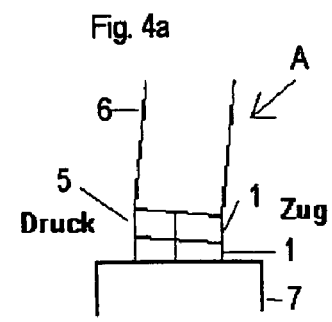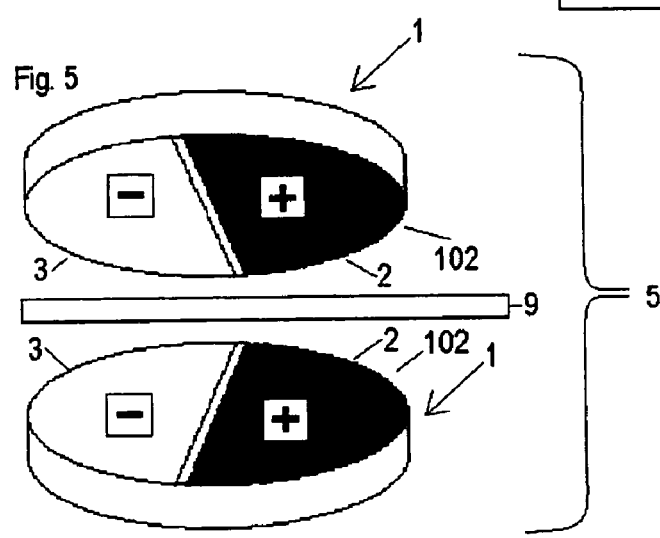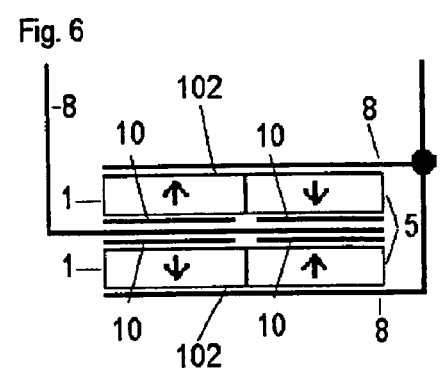

| Kraft | Signal |
|---|---|
| ↓☐↑ | 0 |
| →☐← | 0 |
| ↗☐↙ | 0 |
| ↓☐↑ ↑☐↓ | 2·E |

DEVICE FOR DETERMINING AND/OR MONITORING AT LEAST ONE PHYSICAL PARAMETER AND HAVING A PIEZO-DRIVE FOR OSCILLATION-EXCITATION AND -DETECTION

FIELD OF THE INVENTION

The invention relates to a device for determining and/or monitoring at least one physical parameter of a medium and having at least one mechanically oscillatable unit and at least one drive/receive unit, wherein the drive/receive unit excites the oscillatable unit to oscillate, or, as the case may be, receives the oscillations of the oscillatable unit.

BACKGROUND OF THE INVENTION

The U.S. Pat. Nos. 4,740,726 and 5,247,832 describe a vibratory resonator having an external tube and an internal oscillation rod. A piezoelectric element is secured in each case within a depression on the internal oscillation rod. The rod has a rectangular, elongated shape. The piezoelectric element exerts a bending moment on the rod that leads to wagging movements, given the details of the way in which the rod is embodied.

Disadvantageous in these patents are the special requirements that exist concerning the embodiment of the oscillation rod and the attachment of the piezoelectric element. Furthermore, the oscillation rod does not become excited directly to wagging oscillations, but rather to bending oscillations, which, as a result of the shape of the rod and the attachment of the piezoelectric element, lead to wagging oscillations.

The principle of oscillation-excitation in these patents is as follows: A piezoelectric element is attached to the oscillatable unit, or to a suitable diaphragm, e.g. using an adhesive. When voltage is applied to the piezoelectric element, it undergoes a change in length. Since the piezoelectric element is connected to the oscillatable unit, and the oscillatable unit does not experience an increase in length, the result is that the piezoelectric element and the oscillatable unit bend. With the application of an alternating voltage, a bending-oscillation consequently results. For logical reasons, it must be assured by special details of the oscillatable unit that there is a preferential direction for this oscillation. Furthermore, the piezoelectric element must be attached to the oscillatable unit such that the change in length is transferred essentially into the bending motion. At the same time, the connection must be made so that it still holds when in the bent condition. A preferred method of connection is by means of an adhesive. However, the use of most adhesives is possible only up to a certain temperature.

All in all, this method characterized by the detour through bending oscillations is thus very involved. It requires special measures in respect to the manner in which the piezoelectric element is attached, and in respect to the shape of the oscillatable element. Furthermore, the preferred method of attachment with adhesives is a problem in that such adhesives are applicable only up to a certain temperature. Moreover, it is in principle an unsatisfactory method in that the wagging movement of the oscillatable unit can be achieved only through the intermediate step of the bending oscillation.

SUMMARY OF THE INVENTION

An object of the invention is to provide a device for exciting a mechanically oscillatable unit to oscillate, or, as the case may be, for detecting its oscillation. The device should be as simple and as cost-effective as possible. Such should be the case also with reference to installation and to the development of the other components necessary for the application. Furthermore, the device should enable the oscillations to be directly produced, or directly received, as the case may be, such that a detour through another form of movement need not be taken.

The object of the invention is achieved in a manner such that, in the drive/receive unit, at least one piezo-drive is provided, which has at least one exterior surface composed of at least two segments of different polarization, wherein the directions of polarization are directed essentially opposite to one another, that the mechanically oscillatable unit is directly or indirectly connected to the exterior surface, so that the mechanically oscillatable unit is excited to a movement, or so that a movement of the mechanically oscillatable unit is received, as the case may be, wherein the movement, in each case, is composed of at least two different force components.

The object is likewise achieved according to the invention such that, in the drive/receive unit, at least one piezo-drive is provided, which has at least one exterior surface, by way of which the mechanically oscillatable unit is directly or indirectly connected to the piezo-drive and which is composed of at least two segments, which, through the application of an electric signal to the piezo-drive, exert at least two different force components on the mechanically oscillatable unit, which together lead to a movement of the mechanically oscillatable unit, or which segments, through a movement of the mechanically oscillatable unit, composed of at least two different force components, produce an electric signal in the piezo-drive.

Advantageous and technically the simplest is the embodiment of the invention in which the force components of the movement are directed oppositely to one another, or in which the force components are ones of push and pull, and in which the movement is a wagging movement or a rotary movement.

A great advantage of the invention is that a wagging movement is produced. It is no longer a matter of a bending movement, whose conversion into a wagging movement is realized through the special attachment of the piezo-drive onto a specially-formed rod. This means that the mechanically oscillatable unit can have almost any shape and that the drive can be space-efficient and easily mounted. Furthermore, the costs of an expensive fabrication and preparation are eliminated.

The physical parameters to be determined or monitored can, for example, be the fill level, the viscosity, the density, or the temperature of a medium.

An advantageous embodiment includes that the segments are embodied symmetrically to one another. It can concern, for instance, two halves of a cylinder. The idea is that the segments are quasi short-circuited together, so that e.g. the effects of the forces that act on the side of the piezo-drive are canceled. At the same time, pyroelectric effects are also prevented, so that the drive is also usable in areas where there is danger of explosion.

Advantageous are the embodiments in which the piezo-drive is at least one piezoelectric element or at least one stack composed of piezoelectric elements. Regarding the arrangement of piezoelectric elements in a stack, see for e.g.

the patent DE 198 41 597. The thinner piezoelectric elements have the advantage of being more cost-efficient than e.g. higher cylinders. In order to enable increased force, these elements can be combined suitably into stacks. It is advantageous for this when the piezoelectric elements are arranged in the stack in a such a way that at least two segments of the same polarization are located opposite to, and essentially mutually cover, one another, and that at least one exterior surface results that is composed of at least two segments of different polarization. The same holds true when the piezoelectric elements in the stack lie opposite to one another in such a manner that the segments, which exert or receive the same force components, essentially cover one another, and when there is at least one exterior surface with at least two segments, which exert and receive different force components. This corresponds in each case to an arrangement in which the piezoelectric elements in the stack are connected mechanically in series and electrically in parallel. For the effective use of the piezoelectric elements in the stack, at least one electrically conductive component is provided between them, so that the segments of the exterior surfaces of the piezoelectric elements in the stack are short-circuited with one another, and/or that the exterior surfaces of the piezoelectric elements, which lie opposite to one another in the stack, are short-circuited with one another. In this, a connecting device can be provided so that the piezoelectric elements in the stack are held in compression. Other possibilities for securement are adhesive, solder, and/or weld layers between the elements and/or a screwed connection.

The geometric structure of the piezo-drive is subject to hardly any limitation. It can be disc- or ring-shaped, round or angular. It is only important that an exterior surface results with at least two segments of different polarization, or that an exterior surface results, which can produce at least two different force components. For a cost-favorable and space-saving installation of the piezo-drive, it is possible to provide bores in the piezo-drive for the attachment and/or passage of electrical components, e.g. wires.

In order to produce a wagging movement with the electric signal, or, as the case may be, in order to convert a wagging movement into an electric signal, at least one electrode is provided on the exterior surface of the piezo-drive. This electrode is connected conductively with at least two segments of different polarization, or it is connected with two segments, which exert different force components on the mechanically oscillatable unit, or receive different force components from the mechanically oscillatable unit, as the case may be. Another possibility is, depending on location and the amount of play available in the embodiment, to provide the exterior surface of the piezo-drive with at least one first electrode and at least one second electrode, wherein the first electrode is connected conductively at least with a first segment of a first polarization, and wherein the second electrode is connected conductively at least with a second segment of a second polarization, wherein the first polarization of the first segment is different from the second polarization of the second segment, and wherein the first and second electrodes are connected electrically with one another. Another possibility is that the first electrode is connected conductively at least with a first segment, which exerts and receives a first force component, and that the second electrode is connected conductively at least with a second segment, which exerts and receives a second force component, wherein the first force component of the first segment is different from the second force component of the second segment, and wherein the first and second electrodes are connected electrically with one another. It is, thus, only necessary to enable that different segments of the piezo-drive attain the same signal, with these segments then reacting on account of the signal on the mechanically oscillatable unit with different force components, or, inversely, the signal, which results from the different force components, must be suitably conducted away. For the connection between electrode and piezo-drive, it is reasonable to provide at least one adhesive-, solder-, and/or weld-layer and/or a screwed connection.

A useful embodiment includes, that the piezo-drive has at least two piezoelectric elements or at least two stacks composed of piezoelectric elements or at least one piezoelectric element and at least one stack, wherein one piezoelectric element or one stack serves to excite the mechanically oscillatable unit to oscillate, and wherein a different piezoelectric element or a different stack receives the oscillations of the mechanically oscillatable unit. Thus, here, one part of the piezo-drive serves for exciting the oscillations and a different part serves for receiving the oscillations. A possibility is to install a partition between these two functional sections for mechanical decoupling.

Furthermore, in an advantageous development, at least one adhesive-, solder-, or weld-layer and/or a screwed connection is provided between the piezo-drive and the mechanically oscillatable unit. This connection is for fixing the mechanically oscillatable unit to the drive, and, at the same time, guarantee the transfer of force.

Useful embodiments with features known from, and reliable in, include that the mechanically oscillatable unit is an oscillation fork or a single rod, with the oscillation fork or single rod being secured to a base unit. This can be done, for instance, such that the mechanically oscillatable unit is secured to a diaphragm. The base unit is usually the housing unit, which is secured to the container in which the medium, whose physical parameter is to be determined and/or monitored, is located.

First, applications of the piezo-drive in the case of single rods will be discussed. An embodiment is composed of an internal oscillation rod inside an external tube. The internal rod is secured with one end at a fixing unit in the base unit. This is the secured end of the internal rod. The other end of the internal rod is the free end.

The piezo-drive is advantageously secured within the base unit and thus excites the internal rod, the external tube, or the internal rod and the external tube to oscillate, or else the piezo-drive receives the corresponding oscillations, as the case may be. For this, one embodiment provides that the piezo-drive is connected to the internal rod at the fixing element of the internal rod, with the piezo-drive being attached on the side of the fixing element that is facing, or facing away from, the free end of the internal rod.

A further variation includes that a second fixing element is provided in the base unit, on which the external tube is fixed. This enables the piezo-drive to be secured between the fixing element of the internal rod and the second fixing element of the external tube. Consequently, the piezo-drive can also excite the external tube to oscillate, or, as the case may be, receive its oscillations. This is especially important, for instance, when the external tube is blocked through contact with bulk goods. If, in this case, the design were such that only the internal rod is excited to oscillate, then it could be excited to oscillate despite the blocking of the external tube and this could lead to misinterpretations of the measured results. These misinterpretations are avoided in that the external tube is also excited to oscillate.

Another possibility is that the mechanically oscillatable unit is one in which there is an internal oscillation rod within an external tube, with the external tube being fixed with one end at the base unit and provided at the other end with a cap, and wherein the internal oscillation rod is secured to this cap. Thus, the case here is one of a single rod which is quasi folded-in at one end. This variant presents the opportunity of fixing the piezo-drive between the internal rod and the cap.

Another embodiment is one in which the mechanically oscillatable unit is a single rod with a compensation weight and two bearing points, with one end of the rod being located within a base unit. In such cases, it is useful to have the piezo-drive secured within the base unit behind the compensation weight.

Another class of the mechanically oscillatable units is oscillation forks with two prongs, with both being fixed to the base unit. The base unit can likewise be a diaphragm. Some possibilities for the fixing of the prongs to the base unit are enumerated as follows. Both prongs can be fixed separately to the base unit, e.g. through individual discs. Both prongs can also be fixed through a shared disc. Another possibility is that both of the prongs are fixed within the base unit using a shared U-shaped connection piece. In these embodiments, two piezo-drives are provided, one connected to each prong. Another development having only one piezo-drive results when both prongs are fixed within the base unit using the crossbar of a shared T-shaped connection piece. Then the piezo-drive is installed within the leg of the T-shaped connection piece between the first and second prongs, and only one piezo-drive is sufficient to cause both prongs to oscillate.

The above-mentioned embodiments always concern piezo-drives having, in each case, only two segments of different polarizations or different force components. A further embodiment is one where, on an exterior surface of the piezo-drive, four segments with two different polarizations are provided, or with two force components, as the case may be, wherein the polarizations or force components of the neighboring segments in each case are different. This piezo-drive can likewise be used very effectively with an oscillation fork with two prongs, when in each case the segments with the same polarization, or with the same force component, are positioned over the prongs.

BRIEF DESCRIPTION OF THE DRAWINGS

The invention is explained in greater detail on the basis of the following drawings, which show as follows:

FIG. 1: the fundamental structure of one part of the device;

FIG. 2: a structure of a piezoelectric element having two segments;

FIG. 3: a structure of a piezoelectric element having two segments and one bore;

FIG. 4: the exemplary production of a wagging motion by a stack of two piezoelectric elements;

FIG. 4*a*: an enlarged section of FIG. 4;

FIG. 5: the perspective representation of one kind of arrangement of two piezoelectric elements having two segments in a stack;

FIG. 6: the side view of a stack of two piezoelectric elements with electrodes;

DESCRIPTION OF THE PREFERRED EMBODIMENTS

Figure 7:
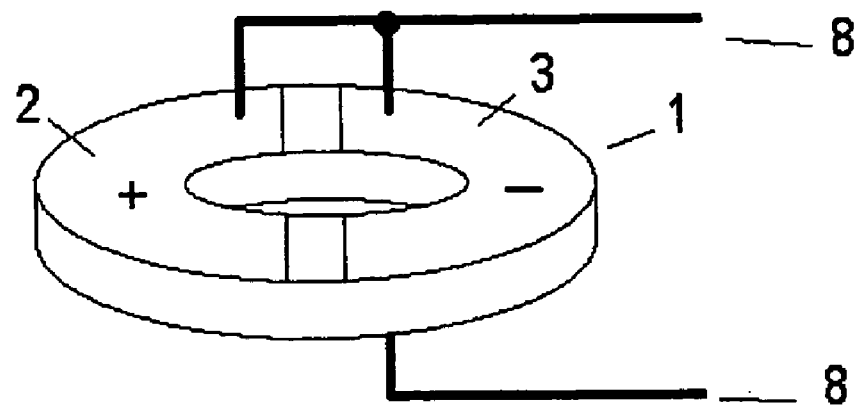
FIG. 7 the illustration of some possible forces on a piezoelectric element and the resulting signals.

FIG. 1 shows the components of concern in the invention for the device for determining and/or monitoring the physical parameter of a medium: mechanically oscillatable unit 100 and drive/receive unit 101. This example uses an oscillation fork 103 as the mechanically oscillatable unit 100. This, however, should not be taken as limiting, because in the following e.g. single rods will also be discussed as the mechanically oscillatable unit 100.

FIGS. 2 and 3 present the structure of an advantageous form of embodiment of a piezoelectric element 1. Shown by way of example is a round disc, whose exterior surface 102 exhibits the two segments 2, 3, whose polarizations are directed opposite to one another (represented here by plus + and minus −). For the passage of components or for the fixing of the element 1, it is possible to provide one or more bores 4 in the disc (FIG. 3). The fact, that here and in the following, the piezo-drives, resp. the piezoelectric elements 1, are represented as round, should not be taken as limiting the generality of the invention. The geometric shape of the piezoelectric elements 1 and of the piezo-drive is subject to no limitation whatsoever. Thus also e.g. angular discs or the like can be used. It is to be ensured only that the mechanically oscillatable unit is connected with at least two segments 2, 3 of different polarization, or different force components.

FIG. 4 shows how, for instance, a stack 5 of two piezoelectric elements 1 excites a single rod 6 directly to wagging-oscillations. The stack 5 is attached to a base unit 7. Three electrically conductive components 8 are located on and in this stack 5. A single rod 6 is connected with the stack 5. The enlarged section (FIG. 4*a*) shows the area around the stack 5. If a voltage is applied to the electrically conductive components 8 (for reasons of clarity, the conductive components are not represented in the enlarged section), then the stack 5 contracts on the one side and expands on the other. Consequently, push and pull forces act on the single rod 6. These two force components lead to the single rod 6 experiencing a direct tilting moment. The resulting wagging motion of this example is executed in a plane that is perpendicular to the connection plane of the stack 5 and the single rod 6. Through the application of an alternating voltage, the single rod 6 oscillates in this plane as specified by the geometry.

FIG. 5 demonstrates how two piezoelectric elements 1 can be arranged so that a stack 5 results to form a piezodrive, such as is represented in FIG. 4. An advantage of the stack 5 is that it results in increased force, through which greater amplitudes can be produced than through the use of thinner piezoelectric elements 1. Furthermore, a stack 5 of flat piezoelectric elements 1 is—up to a certain height— more cost-efficient than a single piezoelectric element 1 of the same height. The two piezoelectric elements 1 are arranged such that always the segments 2, 3 having the same polarization, i.e. having the same force components lie opposite to one another. This can be analogized to two hands clapping. Between both of the elements 1, an electrically conductive component 9 is located, which serves to short-circuit the segments 2, 3 of the elements 1 and the exterior surfaces 102 within the stack 5. A possibility for the electrically conductive element 9 is e.g. a soldering lug.

FIG. 6 is a side view of a stack 5 of two piezoelectric elements 1. The polarizations, or, more accurately, the force components, are indicated here with arrows. Also here, the equal polarizations, or force components, lie opposite to one another. Between the elements 1, an electrode 8 is located, which is connected with the piezoelectric elements 1 by way of the connection elements 10, such as e.g. adhesive, soldered joints, or welds. Alternatively, a device would also be possible in which the piezoelectric elements 1 are held in compression. On both of the exterior surfaces 102 of the stack, two further electrodes 8 are located, which are connected with one another. For the operation of the stack 5 as the piezo-drive, the signs of the voltages applied to the electrodes 8 always alternate, so that an electrically parallel connection results.

FIG. 7 demonstrates a great advantage of the piezoelectric elements of the invention. Represented is one such element 1 having both of the electrodes 8. Below, the effect of different forces (identified by the arrows) on the element is illustrated. Symmetrical forces in each case cancel each other in their effect, and, consequently, produce no signal. Only a wagging movement on the exterior side of the piezoelectric element 1 with the segments 2, 3 of mutually opposing polarizations results in a signal. The wagging movement is a motion which e.g. can be decomposed into the two force components push and pull. The signal is indicated here with 2-E, because, through the forces which act on the piezoelectric element 1 from above and below, an electric potential results that is twice as big as the force of the wagging movement on only one side. Consequently, the piezo-drive is insensitive to most interference forces.

FIGS. 8 through 12 illustrate examples of how the piezo-drive 16 of two segments 2, 3 can, in each case, be used for the oscillation-excitation of a single rod 6. In all of the following figures, the arrows illustrate the acting forces. The forces for the piezo-drives 16 are push and pull; in the case of the mechanically oscillatable units 6 of concern is the wagging motion resulting from the push and pull. At the same time, the positions of the segments 2, 3 of the piezo-drive 16 are also indicated by the arrows. These, however, are only some examples, which are meant to illustrate some preferred embodiments.

Figure 8:
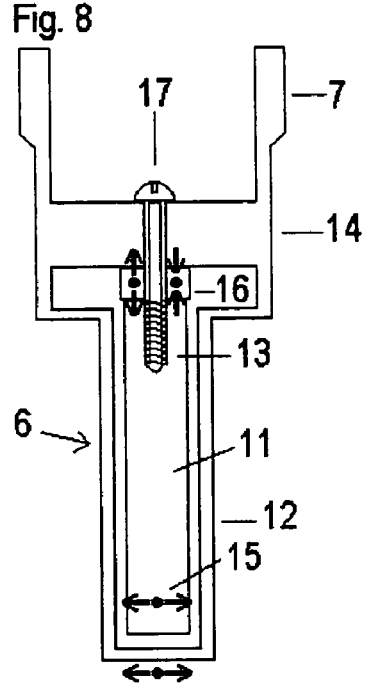
FIG. 8: a single rod as the mechanically oscillatable unit, wherein an internal rod is located in an external tube, and wherein the internal rod is fixed at the secured end of the external tube.
Figure 9:
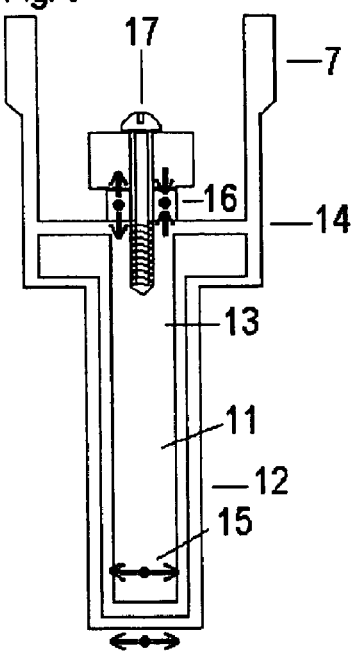
FIG. 9: compared with FIG. 8, another way of securing the piezo-drive.
Figure 10:
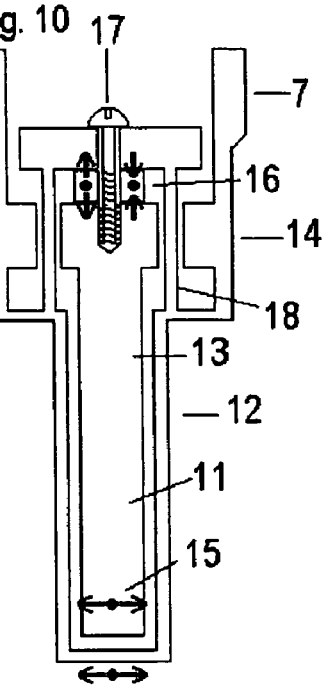
FIG. 10: compared with FIG. 8, a further way of securing the piezo-drive.

FIGS. 8 through 10 show in each case a single rod 6, wherein an internal rod 11 is located inside an external tube 12. One end of the internal rod 11 is secured as the fixed end at a fixing element, e.g. to a diaphragm 14 within the base unit 7. The other end of the internal rod 11 is the free end 15. The piezo-drive 16 is connected with the internal rod 11 at the fixing element 14 by way of a screw connection 17.

In FIG. 8, the piezo-drive 16 is located on the side of the fixing element 14 facing towards the free end 15 of the internal rod 11. In FIG. 9, it is located on the side facing away. In both cases, only the internal rod 11 is excited by the piezo-drive 16 to oscillate. This can be disadvantageous, for instance, when the exterior tube 12 is blocked by bulk goods. In these cases, while the external tube 12 can possibly not oscillate, yet the internal rod 11 can be excited to oscillate, which leads to misinterpretations. In FIG. 10, therefore, the external tube 12 is likewise connected with the piezo-drive 16, by way of the securement unit 18, so that the external tube 12 can likewise be excited to oscillate.

Figure 11:
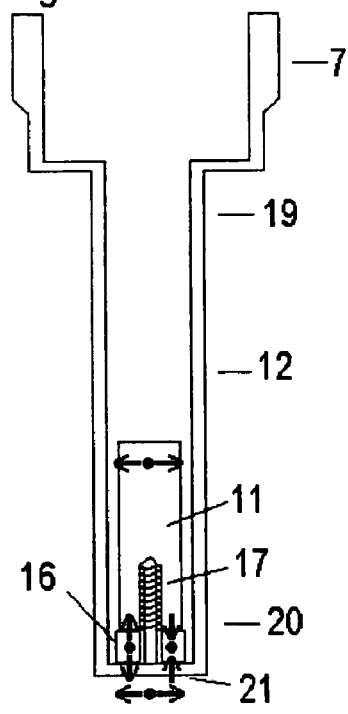
FIG. 11: a single rod as the mechanically oscillatable unit, wherein an internal rod is located in an external tube and is fixed to the end cap of the external tube.

In FIG. 11, the external tube 12 is connected on one end 19 with the base unit 7, and is sealed on the other end 20 with a cap 21. The internal rod 11 and the piezo-drive 16 are fixed to this cap 21 by way of a screw connection 17. Thus, this embodiment is one in which there is a single rod whose end has been quasi folded-in.

Figure 12:
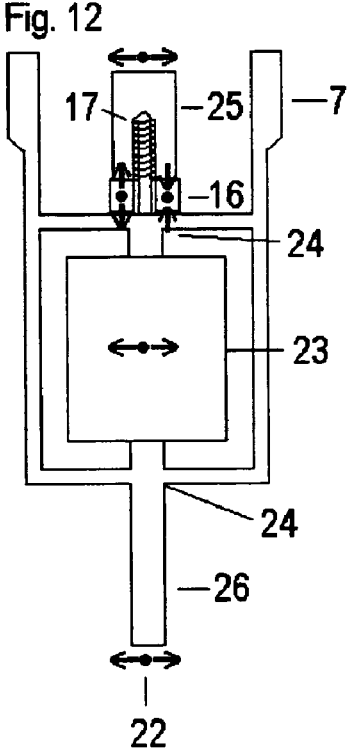
FIG. 12: a single rod with added weight and two bearing points.

FIG. 12 shows a single rod 22 having an additional weight 23, with the single rod 22 having two bearing points 24 in the base unit 7. In this case, the piezo-drive 16 is secured at the end 26 of the single rod 22 located within the base unit 7.

A single rod 6 needs the tilting moment or torque only in its root, i.e. in the area in which it is connected with the base unit 7. For driving an oscillation fork 103 with two prongs 27, a more complicated distribution of forces may be required.

Figure 13:
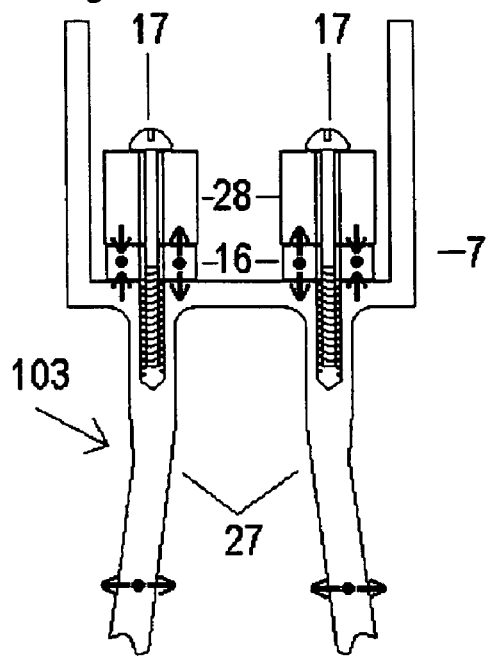
FIG. 13: a fork with two prongs as the mechanically oscillatable unit, with two piezo-drives.
Figure 14:
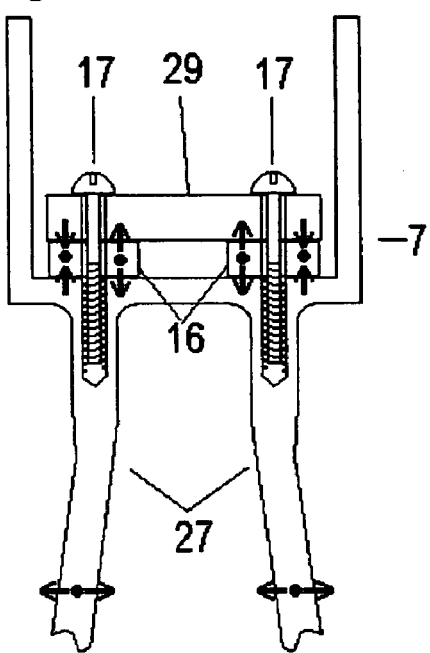
FIG. 14: compared with FIG. 13, another way of fixing the prongs.
Figure 15:
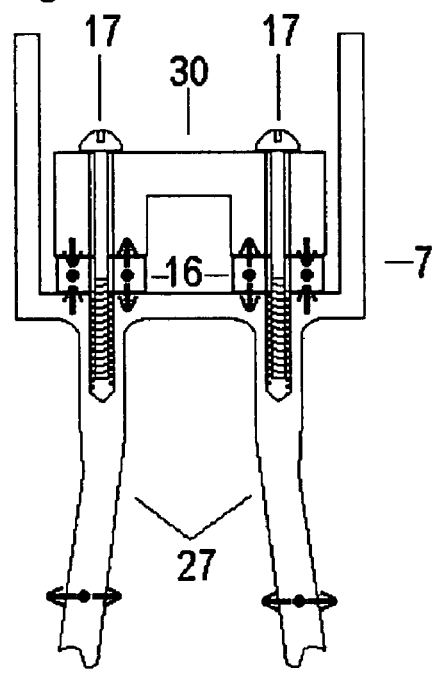
FIG. 15: compared with FIG. 13, a further way of fixing the prongs.

FIGS. 13 through 16 demonstrate embodiments where the mechanically oscillatable units are oscillation forks 103 having two prongs 27. In FIGS. 13 through 15, two piezo-drives 16 are required in each case. The embodiment in FIG. 16 needs only one piezo-drive 16. In these FIGS. 13 to 16, piezo-drives 16 having two segments 2, 3 are provided on an introductory basis. An application of a piezo-drive 16 having more segments may require simple modifications of the embodiment.

Figure 16:
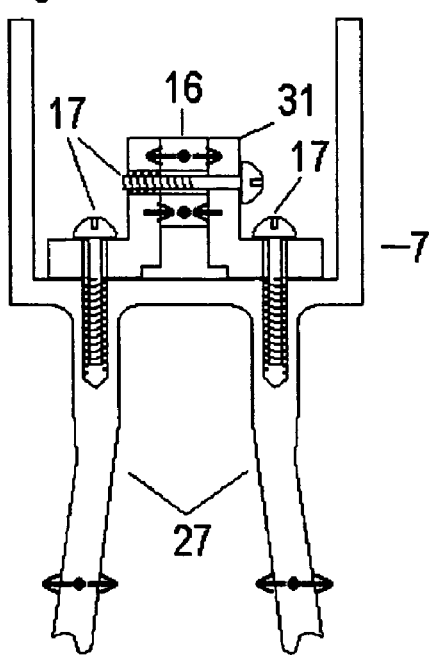
FIG. 16: a fork with two prongs as the mechanically oscillatable unit, with one piezo-drive.

In FIG. 13, each prong 27 is connected to the base unit 7 with a screw connection 17 and separate fixing block 28. In FIG. 14, both prongs 27 are connected to one another within the base unit 7 by way of a shared disc 29. In FIG. 15, the embodiment of the disc 29 as a shared connection piece is extended to a U-shaped connection piece 30. FIG. 16 demonstrates how it is possible to use only one piezo-drive 16 for both prongs 27. For this, the prongs 27 are fixed with a T-shaped connection piece 31, in whose leg the piezo-drive 16 is located, fixed with a further screw connection 17.

Figure 17:
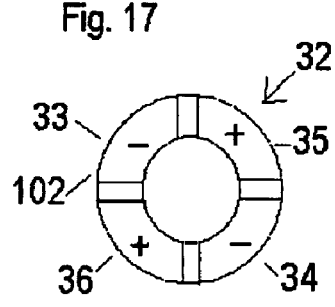
FIG. 17: structure of a piezoelectric element having four segments and one bore.

FIGS. 17 through 20 are devoted especially to the embodiment of a piezo-drive 37 having four segments 33, 34, 35, 36. FIG. 17 shows the exterior surface 102 of a piezoelectric element 32 having four segments 33,34,35,36. The polarizations, or the force components to be produced and received, of the segments 33 and 34, and 35 and 36, are in each case identical. The polarizations, or the force components, of adjoining, neighboring segments alternate.

Figure 18:
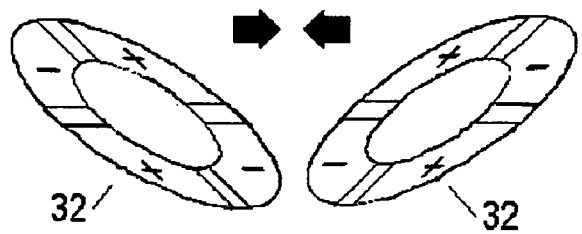
FIG. 18: the perspective representation of a way of arranging two piezoelectric elements having four segments, for a stack.

An especially effective embodiment of the fitting together of two such piezoelectric elements 32 for a stack is shown in FIG. 18. Here again, as in FIG. 4, equal polarizations, or equal force components, lie opposite to one another.

Figure 19:
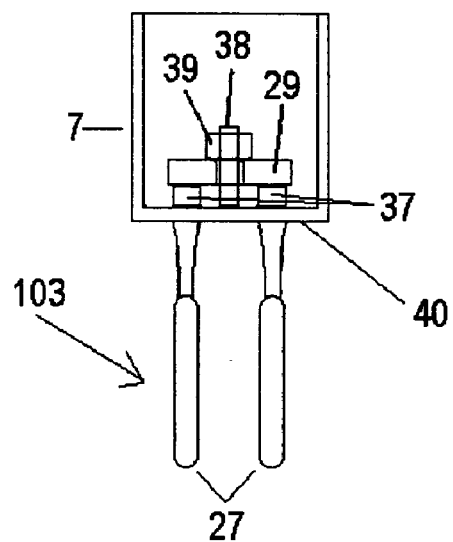
FIG. 19: a fork with two prongs as the mechanically oscillatable unit with one piezo-drive having four segments.
Figure 20:
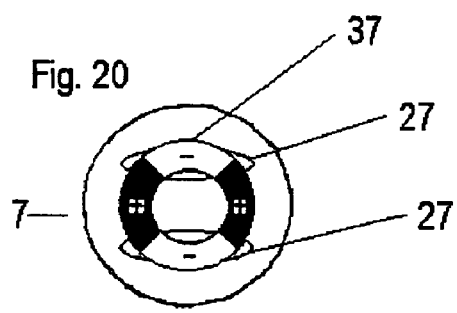
FIG. 20: a section through the assembly of FIG. 19.

FIG. 19 demonstrates the application of such a piezo-drive 37 of four segments for an oscillation fork 103 with two prongs 27 as the mechanically oscillatable unit 100. These prongs 27 are fixed on a diaphragm 40 of the base unit 7. Within the base unit 7, a piezo-drive 37 having four segments is secured on the diaphragm 40. FIG. 20 shows that the segments with the same polarization (here minus), or the same force components, are in each case located above the prongs 27.

Further embodiments of the mechanically oscillatable unit, of the piezo-drive, and of the manner of connection of the unit with the drive can be suitably fabricated according to requirement and opportunities.

LIST OF REFERENCE CHARACTERS 1 piezoelectric element having two segments
2 segment
3 segment
4 bore
5 stack
6 single rod
7 base unit
8 electrode
9. electrically conductive component, soldering lug
10 connection element
11 internal rod
12 external tube
13 secured end
14 fixing element
15 free end
16 piezo-drive
17 screw connection
18 securement unit in the base unit
19 secured end
20. free end
21 cap
22 single rod
23 additional weight
24 bearing point
25 end within the base unit
26. end outside of the base unit
27 prongs
28 fixing block
29 disc
30 U-shaped connection piece
31 T-shaped connection piece
32 piezoelectric element having four segments
33 segment
34 segment
35 segment
36 segment
37 piezo-drive having four segments
38 fixed bolt
39 nut
40 diaphragm
100 mechanically oscillatable unit
101 drive/receive unit
102 exterior surface
103 oscillation fork

The invention claimed is:

1. A device for determining and/or monitoring at least one physical parameter of a medium having:
   at least one mechanically oscillatable unit; and
   at least one drive/receive unit, wherein:
   said drive/receive unit excites said mechanically oscillatable unit to oscillate, or
   said drive/receive unit receives the oscillations of said oscillatable unit;
   said drive/receive unit is provided with at least one piezo-drive, which has at least one exterior surface, said at least one pieze-drive which is composed of at least two segments having different polarizations with the directions of polarization being directed essentially opposite to one another;
   said mechanically oscillatable unit is directly or indirectly connected with said exterior surface, so that said mechanically oscillatable unit is excited to a movement, or so that a movement of said mechanically oscillatable unit is received, with the movement in each case being composed of at least two different force components, and
   the force components are ones of push and pull, and the movement is a wagging movement or rotary movement in a plane which is perpendicular to said at least one exterior surface of said piezo-drive.

2. The device as claimed in claim 1, wherein:
   the force components of the movement are essentially opposite to one another.

3. The device as claimed in claim 1, wherein:
   said segments are embodied symmetrically to one another.

4. The device as claimed in claim 1, wherein:
   said piezo-drive comprises at least one piezoelectric element or at least one stack composed of piezoelectric elements.

5. The device as claimed in claim 4, wherein:
   said stack comprises at least two piezoelectric elements which are arranged in such a way that a force amplification results.

6. The device as claimed in claim 5, wherein:
   said piezoelectric elements in said stack are arranged in such a way that they are connected mechanically in series and electrically in parallel.

7. The device as claimed in claim 5, wherein:
   at least one electrically conductive component is provided between said piezoelectric elements in said stack.

8. The device as claimed in claim 5, wherein:
   the segments of the exterior surfaces of said piezoelectric elements in said stack are short-circuited with one another; and/or
   the exterior surfaces of said piezoelectric elements which lie opposite to one another in said stack are short-circuited with one another.

9. The device as claimed in claim 5, wherein:
   a connecting device is provided so that said piezoelectric elements in said stack are held in compression.

10. The device as claimed in claim 5, wherein:
    at least one adhesive-, solder-, or weld-layer and/or screwed connection is provided between said piezoelectric elements in said stack.

11. The device as claimed in claim 1, wherein:
    at least one electrode is provided on the exterior surface of said piezo-drive and connected conductively with at least two segments of different polarization, or connected conductively with at least two segments which exert and receive different force components.

12. The device as claimed in claim 1, wherein:
    said piezo-drive comprises at least two piezoelectric elements, or at least two stacks composed of piezoelectric elements or at least one piezoelectric element and at least one stack, said one piezoelectric element or one stack serves to excite said mechanically oscillatable unit to oscillate, and another piezoelectric element or another stack receives the oscillations of said mechanically oscillatable unit.

13. The device as claimed in claim 1, wherein:
said mechanically oscillatable unit comprises an oscillation fork or a single rod, said oscillation fork or single rod being secured to a base unit.

14. The device as claimed in claim 13, wherein:
said mechanically oscillatable unit comprises an oscillation fork with first and second prongs, said first and second prongs being fixed to said base unit.

15. The device as claimed in claim 14, wherein:
said piezo-drive is connected within said base unit with said two prongs such that in each case the segments of the same polarization, or having the same force components, are positioned over said prongs.

16. The device as claimed in claim 1, wherein:
a piezo-drive is provided, which has at least one exterior surface, having four segments of two different polarizations, with the polarizations of neighboring segments are always different, or having four segments, which exert and receive two different force components, with the force components of neighboring segments are always different.

17. A device for determining and/or monitoring at least one physical parameter of a medium having:
at least one mechanically oscillatable unit; and
at least one drive/receive unit, wherein:
said drive/receive unit excites said oscillatable unit to oscillate, or
said drive/receive unit receives the oscillations of said oscillatable unit;
said drive/receive unit is provided with at least one piezo-drive, which has at least one exterior surface, b way of which said having at least two segments, which, by the application of an electric signal to the piezo-drive, exert at least two different force components on said mechanically oxcillatable unit, which together lead to a movement of said mechanically oscillatable unit, or which, through a movement of said mechanically oscillatable unit composed of at least two different force components, produce an electric signal in said piezo-drive, and
the force components are ones of push and pull, and the movement is a wagging movement in a plane which is perpendicular to said at least one exterior surface of said piezo-drive.

18. A device for determining and/or monitoring at least one physical parameter of a medium having:
at least one mechanically oscillatable unit; and
at least one drive/receive unit, wherein:
said drive/receive unit excites said mechanically oscillatable unit to oscillate, or
said drive/receive unit receives the oscillations of said oscillatable unit;
said drive/receive unit is provided with at least one piezo-drive, which has at least one exterior surface, said at least one pieze-drive which is composed of at least two segments having different polarizations with the directions of polarization being directed essentially opposite to one another; and
said mechanically oscillatable unit is directly or indirectly connected with said exterior surface, so that said mechanically oscillatable unit is excited to a movement, or so that a movement of said mechanically oscillatable unit is received, with the movement in each case being composed of at least two different force components, wherein:
said mechanically oscillatable unit comprises an oscillation fork or a single rod, said oscillation fork or single rod being secured to a base unit;
said mechanically oscillatable unit further comprises an internal oscillation rod within an external tube;
said external tube is fixed with one end at said base unit and provided at the other end with a cap; and
said internal oscillation rod is secured to said cap.

19. A device as claimed in claim 18, wherein:
said piezo-drive is fixed between said internal rod and said cap.

* * * * *